(12) United States Patent
Grunhut

(10) Patent No.: US 8,696,628 B2
(45) Date of Patent: Apr. 15, 2014

(54) AUTOMATIC INJECTION DEVICE

(75) Inventor: Guillaume Grunhut, Grenoble (FR)

(73) Assignee: Becton Dickinson France, Le Pont de Claix (FR)

( * ) Notice: Subject to any disclaimer, the term of this patent is extended or adjusted under 35 U.S.C. 154(b) by 269 days.

(21) Appl. No.: 13/120,676

(22) PCT Filed: Sep. 29, 2008

(86) PCT No.: PCT/IB2008/003290
§ 371 (c)(1),
(2), (4) Date: May 19, 2011

(87) PCT Pub. No.: WO2010/035060
PCT Pub. Date: Apr. 1, 2010

(65) Prior Publication Data
US 2012/0116319 A1    May 10, 2012

(51) Int. Cl.
*A61M 5/20* (2006.01)
*A61M 5/00* (2006.01)
*A61M 5/32* (2006.01)

(52) U.S. Cl.
USPC ........... 604/135; 604/110; 604/131; 604/134; 604/187; 604/198

(58) Field of Classification Search
CPC ............... A61M 2005/206; A61M 2005/2073; A61M 2005/208; A61M 5/2033; A61M 5/326; A61M 5/3287
USPC ......... 604/110, 117, 134, 135, 157, 187, 192, 604/198, 208, 218, 228, 234, 240, 131, 151
See application file for complete search history.

(56) References Cited

U.S. PATENT DOCUMENTS

| | | |
|---|---|---|
| 2005/0222539 A1 | 10/2005 | Gonzales et al. |
| 2005/0277886 A1 | 12/2005 | Hommann et al. |
| 2006/0173408 A1 * | 8/2006 | Wyrick .......................... 604/110 |
| 2007/0021720 A1 | 1/2007 | Guillermo |
| 2011/0245770 A1 | 10/2011 | Carrel et al. |

FOREIGN PATENT DOCUMENTS

| | | |
|---|---|---|
| WO | 2004060445 A2 | 7/2004 |
| WO | 2005/044347 A1 | 5/2005 |
| WO | 2006052737 A1 | 5/2006 |
| WO | 2007/132353 A2 | 11/2007 |
| WO | 2008/029280 A2 | 3/2008 |

* cited by examiner

*Primary Examiner* — Kami A Bosworth
*Assistant Examiner* — Imani Hayman
(74) *Attorney, Agent, or Firm* — Hoffman & Baron, LLP

(57) ABSTRACT

The present invention relates to a device for automatic injection of a product comprising a container, a needle and a piston. The device includes a housing receiving the container, the container being movable with respect to the housing between an initial position and an insertion position, distally spaced relative to the initial position; a safety shield coupled to the housing and movable with respect thereto between a rest position, an activation position, proximally spaced relative to the rest position, and a safety position, distally spaced with respect to the rest position; biasing feature for causing the movement of the safety shield to the safety position; triggering feature for causing the container to move from its initial position to its insertion position, the triggering feature being releasable by movement of the safety shield to the activation position; and, isolating feature for isolating the safety shield from the biasing feature when the safety shield is moved to its activation position.

5 Claims, 3 Drawing Sheets

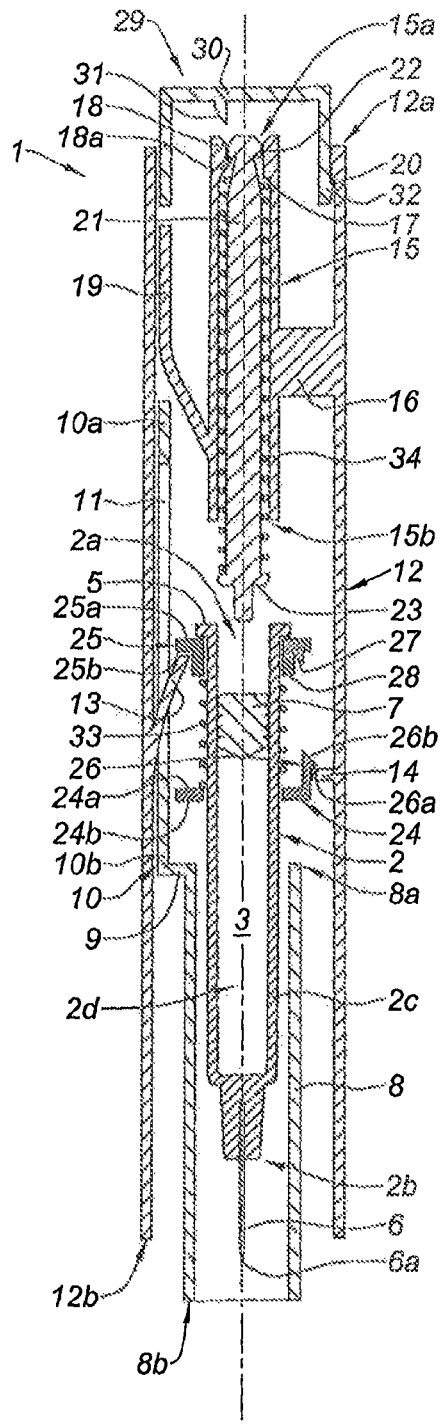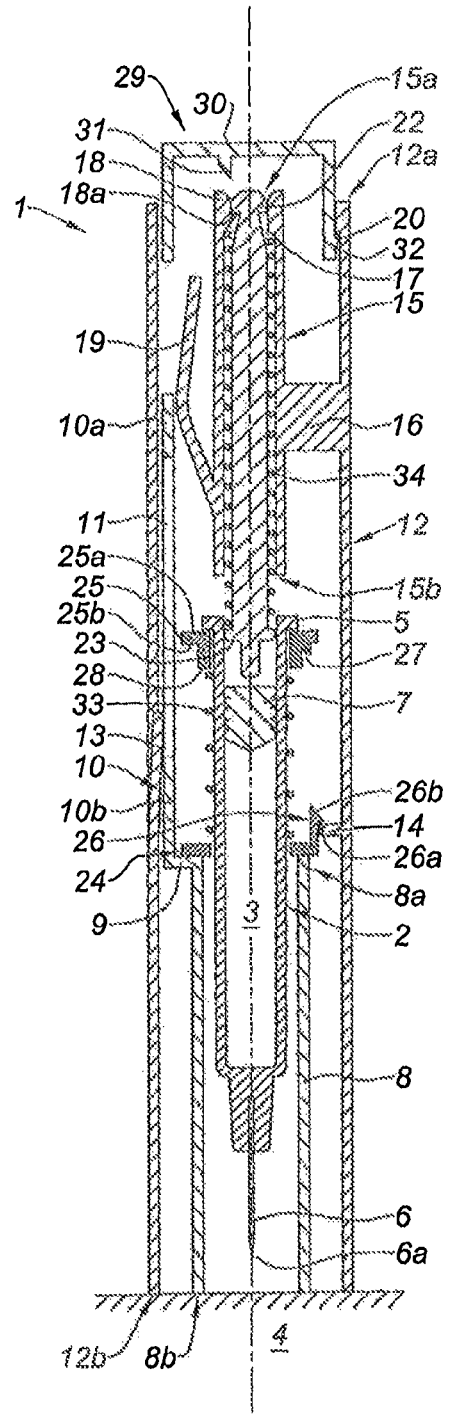

AUTOMATIC INJECTION DEVICE

Figure 3:
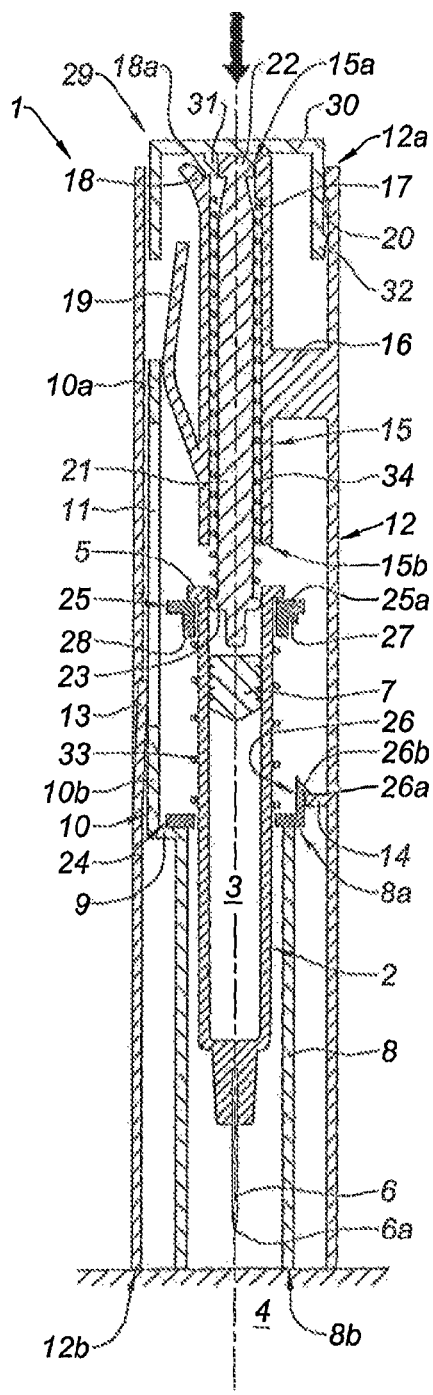

The present invention relates to a device for automatic injection of a product, especially for self-injection, so that the use of the device is as atraumatic as possible for the patient.

In this application, the distal end of a component or of a device is to be understood as meaning the end furthest from the user's hand and the proximal end is to be understood as meaning the end closest to the user's hand. Likewise, in this application, the "distal direction" is to be understood as meaning the direction of injection, and the "proximal direction" is to be understood as meaning the opposite direction to the direction of injection.

Some illnesses necessitate regular injections of drugs or products, for instance on a daily basis. In order to simplify the treatment, some self-injectors have been provided in order to allow the patient to perform the injection on its own.

Of course, since the patient is usually neither a nurse nor an educated person in medical devices, such self-injectors must prove to be very simple to use and also very safe. In particular, the insertion of the needle must be performed at the right depth, the correct dose of product must be injected, that is to say a complete injection must be performed, and the injector must be deactivated after use before it is disposed of. Preferably, the needle should not be exposed, before and after use, in order to prevent any accidental needlestick injury. Usually, such self-injectors are provided with a safety shield in order to protect the needle before use and after use.

Another important requirement of these self-injection devices is that they must not be able to be activated inadvertently, before the patient is ready to perform the injection, and in particular before the device is correctly applied at the right injection site.

Such self-injectors with automatic insertion and injection steps, and a safety shield in order to protect the needle after use have been described in document WO2007/132353. This document describes a device for automatic injection in which the injection cannot be triggered before the device is correctly in place. In particular, the user needs to push distally on an external housing of the device, once the device is applied on the injection site, in order to be allowed to trigger the injection. Nevertheless, in order to complete this step, the user has to overcome the force of biasing means intended to cause the automatic extension of the safety shield after use. The force of these biasing means is usually high and the consequence is that the user may be hurt or may feel a bad sensation on the skin when accomplishing the step of pushing distally on the external housing of the device for placing the device correctly and being allowed to trigger the injection. This bad feeling may refrain the user/patient from carrying on the administration of the product.

There is therefore a need for an automatic injection device that would be safe but at the same time would allow the user/patient to put the device correctly in place without feeling badly or feeling too high a pressure on the skin at the injection site.

The present invention meets this need by proposing a device for automatic injection of a product into an injection site, said device comprising a safety system for preventing the triggering of the injection when the device is not correctly placed on the site of injection, a safety shield capable of being deployed automatically at the end of injection under the effect of biasing means, and means for cancelling the force of said biasing means felt by the patient when said user/patient completes the step of deactivating the safety system.

The present invention relates to a device for automatic injection of a product into an injection site, the product being carried by a container having an open proximal end and a substantially closed distal end and carrying a needle to provide an outlet port for the product from the container, and a piston provided in the container and movable with respect to the container, the movement of the piston causing the product to be expelled from the container through the needle, a housing receiving at least partially said container, said container being movable with respect to said housing between an initial position, in which a tip of the needle does not extend beyond a distal end of said housing, and an insertion position, distally spaced relative to said initial position, and in which the tip of the needle extends beyond said distal end of said housing, a safety shield coupled to said housing and movable with respect thereto between a rest position, an activation position, proximally spaced relative to said rest position, and a safety position, distally spaced with respect to said rest position, biasing means for causing the movement of said safety shield to said safety position, triggering means for causing the container to move from its initial position to its insertion position, said triggering means being releasable by movement of said safety shield to said activation position, characterized in that said device further comprises:

isolating means for isolating said safety shield from said biasing means when said safety shield is moved to its activation position.

The device of the invention provides for a very safe device, which cannot be triggered as long as it is not correctly located at the injection site and which does not hurt the user during the step of deactivating the safety system, said safety system being formed by the fact that the triggering means cannot be activated as long as the safety shield has not moved from its rest position to its activation position. Moreover, in the device of the invention, the needle is automatically protected after use thanks to biasing means deploying the safety shield. In particular, because of the presence of specific isolating means in the device of the invention, the patient does not feel the force of the biasing means during the step of moving the safety shield from its rest position to its activation position.

In an embodiment of the invention, said isolating means comprise a first ring, receiving said container, said first ring being coupled to said biasing means in the proximal direction and coupled to said housing in the distal direction, and being independent from said safety shield, at least when said safety shield is moved to its activation position.

In the present application, by the expression "A is coupled to B in the X direction", one means that A is linked to B when A is moved in the X direction: in other words, when A is coupled to B in the X direction, then if A is caused to move in the X direction, then B is also caused to move in the X direction.

In the present application, by the expression "A is free or independent from B", one means that A is not coupled to B.

In an embodiment of the invention, said first ring comprises at least a flexible tooth provided with a distal abutment surface and said housing comprises at least a radial stop, said first ring being coupled to said housing in the distal direction by means of said distal abutment surface resting on said radial stop, when said safety shield is moved to its activation position.

In an embodiment of the invention, said device further comprises a second ring, said second ring being fixed to the proximal region of said container and being proximally spaced with respect to said first ring when said safety shield is moved to its activation position, said biasing means comprising a helical spring, a proximal end of said helical spring bearing on a part of said second ring and a distal end of said helical spring bearing on a part of said first ring.

In an embodiment of the invention, said flexible tooth comprises a proximal sloping surface and said second ring comprises a distal sloping surface, said distal sloping surface being capable to come in abutment against said proximal sloping surface so as to deflect said flexible tooth and disengage said flexible tooth from said radial stop, thereby freeing said first ring from said housing when said container is in its insertion position.

In an embodiment of the invention, said safety shield comprises at least one radial rim, said radial rim being located in regards to the distal face of said first ring, said distal face of said first ring coming in abutment against said radial rim when said container is in its insertion position, thereby coupling said first ring to said safety shield in the distal direction under the biasing force of the biasing means.

Figure 4:
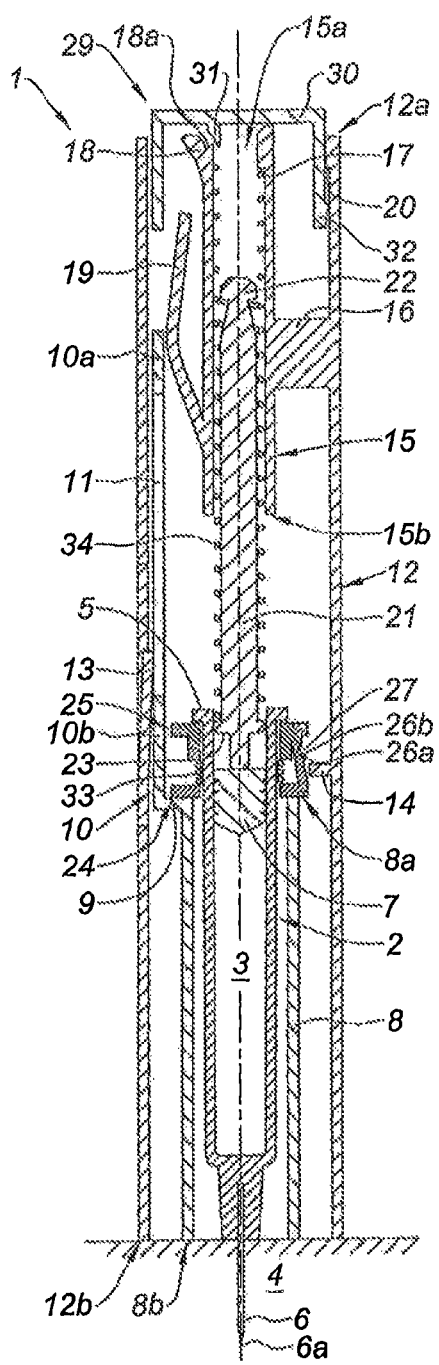
Figure 5:
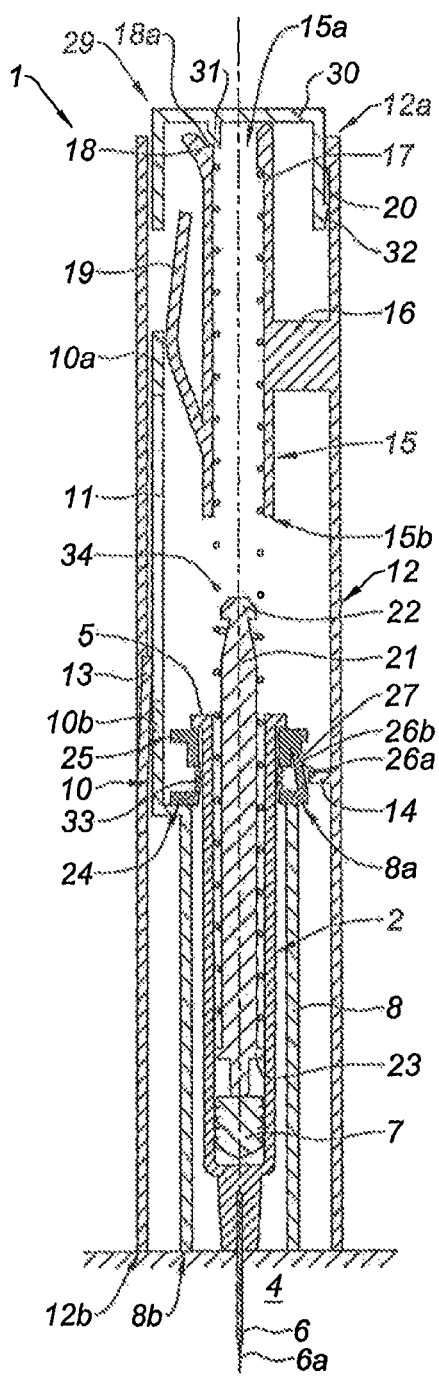

The device of the invention will now be further described in reference to the following description and attached drawings in which:

FIG. 1 is a longitudinal cross section view of an embodiment of the device of the invention before use, FIG. 2 is a longitudinal cross section view of the device of FIG. 1, after deactivation of the safety system, FIG. 3 is a longitudinal cross section view of the device of FIG. 1 at the time of activation of the triggering means, FIG. 4 is a longitudinal cross section view of the device of FIG. 1 once the container is in its insertion position, FIG. 5 is a longitudinal cross section view of the device of FIG. 1 at the end of injection.

Referring now to the drawings, the present invention will now be described in detail. FIG. 1 shows a longitudinal cross section view of a device for automatic injection according to an embodiment of the present invention and generally designated by reference number 1. The device 1 of the invention comprises a container 2 carrying a product 3 to be injected into an injection site 4 (see FIGS. 2-5). The container 2 has an open proximal end 2a provided with a flange 5 and a substantially closed distal end 2b bearing an injection needle 6. Lateral walls 2c of the container 2 extend between the proximal and distal ends (2a, 2b) and define a reservoir 2d sized and shaped to contain a predetermined amount of a product 3 for injection. The injection needle 6 may be fixed to the distal end 2b of the container 2, or removable therefrom, as a matter of design choice. The injection needle 6 is in fluid communication with the reservoir 2d and provides an outlet port for the product 3 from the container 2. A piston 7 is provided in the container and movable with respect to the container 2: as will appear from FIG. 5, the distal movement of the piston 7 is intended to cause the product 3 to be expelled from the container 2 through the needle 6. A needle shield (not represented) may be provided at the distal end 2b of the container 2 to cover and protect the needle 6 before use of the device 1.

The device 1 of FIGS. 1-5 further comprises a safety shield 8 receiving at least partially said container 2. On the example shown, the safety shield 8 has a general tubular shape with an open proximal end 8a and an open distal end 8b. The proximal end 8a of the safety shield 8 is provided with at least one radial rim 9 prolonged by a longitudinal leg 10 extending in the proximal direction. The longitudinal leg 10 is provided with a window 11 separating a proximal portion 10a of said leg 10 from a distal portion 10b of said leg 10.

The device 1 of FIGS. 1-5 further comprises a housing 12 receiving at least partially said container 2 and said safety shield 8. On the example shown, the housing 12 has a general tubular shape with an open proximal end 12a and an open distal 12b.

The housing 12 is provided on its internal wall with at least a flexible leg 13 extending in the proximal direction. The flexible leg 13 is capable of being deflected from a free position in which it extends radially inwardly (see FIG. 1), to a stressed position in which it extends longitudinally parallel to the walls of the housing 12 (see FIG. 2).

The housing 12 further comprises a radial stop 14 located on the internal wall of said housing 12.

In its proximal region, the housing 12 is further provided with an inner cylinder 15 linked to the housing 12 via a radial wall 16. The inner cylinder 15 has an open proximal end 15a and an open distal end 15b. The cylinder 15 is provided at its proximal end 15a with at least an inner radial rim 17 and with at least a flexible tooth 18 provided with a proximal abutment surface 18a.

The inner cylinder 15 is provided on its outer wall with a flexible tongue 19 extending in the proximal direction. The flexible tongue 19 is capable of being deflected from a free position, in which it extends radially outwardly with respect to the inner cylinder 15 (see FIG. 1) and a stressed position, in which it extends longitudinally, parallel to the walls of the inner cylinder 15 (see FIG. 2).

At its proximal end 12a, the housing 12 is provided on its inner wall with a radial abutment surface 20.

As will appear from the following description of FIGS. 1-5, the container 2 is movable with respect to said housing 12 between an initial position, in which a tip 6a of the needle 6 does not extend beyond a distal end 12b of said housing (see FIGS. 1-3) and an insertion position, distally spaced relative to said initial position, in which the tip 6a of the needle 6 extends beyond said distal end 8b of said safety shield 8 (see FIG. 4).

The device 1 of FIGS. 1-5 is further provided with a piston rod 21 intended to push distally the piston 7 in order to expel the product 3 out of the container 2 and realise the injection. On the example shown, the piston rod 21 is provided at its proximal end with a radial stop 22 and at its distal end with a radial flange 23.

The device 1 of FIGS. 1-5 further comprises a first ring 24 and a second ring 25, both rings (24, 25) receiving the container 2. The second ring 25 is proximally spaced with respect to said first ring 24.

The first ring 24 has a proximal face 24a and a distal face 24b. The first ring 24 further comprises a flexible tooth 26, extending in the proximal direction from the proximal face of said first ring 24, said flexible tooth 26 being provided with a distal abutment surface 26a and with a proximal sloping surface 26b. As shown on FIGS. 1 and 2, before the insertion step, the distal abutment surface 26a of the first ring 24 rests on the radial stop 14 of the housing 12.

The second ring 25 is fixed to the flange 5 of the container 2 by classical fixation means (not shown) such as clips, glue, etc. . . . The second ring 25 has a proximal face 25a and a distal face 25b. The second ring 25 is further provided with a distal sloping surface 27 and with a distal skirt 28.

The device 1 of FIGS. 1-5 further comprises a push button 29 partially received within the distal region of the housing 12. The push button 29 has the general shape of a tube closed at its proximal end by a pushing wall 30 and open at its distal end. The pushing wall comprises on its inner face a peg 31 extending distally. The pushing button 29 is provided at its distal end with an outer projection 32.

A first helical spring 33 is provided around the container 2 and between the first ring 24 and the second ring 25. As shown on FIG. 1, the proximal end of the first helical spring 33 bears on the distal skirt 28 of the second ring 25 and the distal end of the first helical spring 33 bears on the proximal face 24a of the first ring 24.

A second helical spring 34 is provided around the piston rod 21. As shown on FIG. 1, the proximal end of the second helical spring 34 bears on the inner radial rim 17 of the inner cylinder 15 and the distal end of the second helical spring 34 bears on the proximal face of the flange 23 of the piston rod 21.

As will appear from the following description, the safety shield 8 is coupled to said housing 12 and movable with respect thereto between a rest position, an activation position, proximally spaced relative to said rest position, and a safety position, distally spaced with respect to said rest position. As will also appear from the description, the push button 29 is intended to be used as triggering means for activating the injection, said triggering means being releasable by movement of said safety shield 8 to its activation position.

The functioning of the device 1 will now be explained in reference to FIGS. 1-5. Before providing a detailed description of the operation of a device 1 constructed in accordance with the present invention, the following general description of its operation is provided. The inventive device 1 is provided to a user ready-to-use. The container 2 is filled with a predetermined dose of an injectable product 3. At the time of use, the user places the device 1 against his/her skin at an injection site 4 and applies a distal force on the housing 12. As the housing 12 is pressed distally, the safety shield 8 is caused to move in the proximal direction and into the housing 12. Due to a safety system of the inventive device 1, a user cannot activate the device 1 (i.e., cause the container 2 to move from its initial position to its insertion position) until the safety shield 8 is caused to move a predetermined distance in the proximal direction with respect to the housing 12. Indeed, the container 2 is in a passive state, ie is not allowed to move from its initial position to its insertion position, as long as the safety shield 8 has not moved on said predetermined distance. With the device 1 pressed against his/her skin (and the safety shield 8 moved on said distance in the proximal direction), the container 2 adopts an active state, and the user can activate the device 1 and press the push button 29. That will cause the container 2 to move from its initial position to its insertion position, which also causes the needle 6 to pierce the user's skin. The injection may then be realised. Once the injection is complete, the user removes the device 1 from the injection site and the safety shield 8 is caused to automatically extend from the housing 12 to cover the now-contaminated tip 6a of the needle 6. Advantageously, even if the user removes the device 1 from the injection site 4 before the injection is complete, the safety shield 8 will automatically extend over the tip of the needle. Once the device 1 is removed from the injection site 4 and the shield 8 is extended over the tip of the needle 6, the shield 8 locks in place and cannot thereafter be moved from its locked position in the proximal direction to expose the tip 6a of the needle 6. The used device 1 is thus rendered safe for handling and disposal.

On FIG. 1 is shown the device 1 before use, as provided to the user. In this position, the flexible leg 13 of the housing is in its free position and extends radially inwardly: as shown on FIG. 1, said flexible leg 13 therefore protrudes through the window 11 of the longitudinal leg 10 of the safety shield 8 and engages the distal face 25b of the second ring 25. The container 2 is by consequence in a passive state: it cannot move distally. Moreover, in the before use position of FIG. 1, the flexible tongue 19 of the inner cylinder 15 is also in its free position: that is to say that said flexible 19 extends radially outwardly with respect to said cylinder 15. As shown on FIG. 1, in this position, said flexible tongue 19 faces the distal end of the push button 29. Thus, if the user pushes on the push button 29, the distal end of the push button 29 abuts on the flexible tongue 19 and the distal movement of the push button 29 is stopped before the peg 31 reaches the flexible tooth 18 of the inner cylinder 15. The triggering means, ie the push button 29, is therefore in a locked position and cannot be released. As shown on FIG. 1, said flexible tooth 18, by its proximal abutment surface 18a being engaged in the radial stop 22 of the piston rod 21, prohibits any freeing of the second helical spring 34: the movement of the container 2 to its insertion position is not possible. In consequence, in the position of FIG. 1, the injection cannot be activated. The device 1 of the invention is particularly safe and cannot be activated as long as it is not correctly placed on the injection site. The flexible tongue 19 and the flexible leg 13 contribute to the ability of the device 1 to adopt a locked position and therefore form part of the safety system of the device of the invention.

In the position shown on FIG. 1, the first helical spring 33 is in a partially compressed state and the second helical spring 34 is in a compressed state. As appears from FIG. 1, the first helical spring 33 is compressed between the first ring 24 and the second ring 25. Moreover, the first ring 24 is in abutment on the radial stop 14 of the housing 12 by means of the distal abutment face 26a of said first ring 24 resting on said radial stop 14. As a consequence, in this before use position as shown on FIG. 1, the safety shield 8 is not coupled to the first helical spring 33: in other words, the safety shield 8 is independent and free from said first helical spring 33. The first ring 24 therefore acts as an isolating means for isolating or freeing said safety shield 8 from said first helical spring 33. The safety shield 8 is thus allowed to move with respect to the housing 12 without interacting with the first helical spring 33.

In this position of the device 1, the tip 6a of the needle 6 is protected by the housing 12 whose distal end 12b extends beyond said tip 6a of the needle 6. In this position of the device 1 also, the safety shield 8 is in a rest position.

When the user wishes to proceed with the administration of the product 3, he applies the device 1 on the skin of the patient at the injection site 4 and pushes the housing 12 distally, as shown on FIG. 2, thereby causing the safety shield 8 to move with respect to said housing 12 from its rest position to an activation position, proximally spaced relative to said rest position. During this step, as explained hereinabove, the first ring 24 is coupled to the biasing means, ie the helical spring 33, in the proximal direction and coupled to the housing 12 in the distal direction by means of said distal abutment surface 26a resting on said radial stop 14, and it is independent or isolated from said safety shield 8. As a consequence, the safety shield 8 is free or isolated from the first helical spring 33 and it does not interact with said first helical spring 33. The patient has therefore no bad feeling on the skin: the patient does not feel the force of the first helical spring 33. The patient feels better at ease and is not hurt during this step. This contributes to a safer use of the device 1 for the patient/user.

As shown on FIG. 2, while the user/patient has pushed distally on the housing 12, the safety shield 8 has moved proximally with respect to the housing 12. As a consequence, the distal part 10b of the longitudinal leg 10 has come in abutment on the flexible leg 13 of the housing 12 and has put it under stress, forcing it to deflect so as to reach a position parallel to the wall of the housing 12, as shown on FIG. 2. The flexible leg 13 of the housing 12 has therefore disengaged from the distal face 25b of the second ring 25. At the same time and as a consequence of the same movement, the proximal part 10a of the longitudinal leg 10 of the safety shield 8 has come in abutment on the flexible tongue 19 of the inner cylinder 15 and has deflected it, forcing it to reach a position where said flexible tongue 19 is parallel to the wall of the inner cylinder 15: as shown on FIG. 2, in this position, the flexible tongue 19 no longer faces the distal end of the push button 29.

The push button 29 is linked to the housing 12 by means of its outer projection 32 being engaged in the radial abutment surface 20 of the housing 12; such an engagement allows the push button 29 to move distally with respect to the housing if a user exerts a distal pressure on the pushing wall 30 of the push button.

As appears clearly from FIG. 2, the device 1 and/or the container 2 are now in their active state: the flexible leg 13 is disengaged and the flexible tongue 19 is also disengaged. The safety shield 8 is now in its activation position. The triggering means, ie the push button 29, may now be released and insertion of the container 2 can be triggered.

In order to trigger the insertion of the container 2, the user pushes distally on the pushing wall 30 of the push button 29 which acts as triggering means. As shown on FIG. 3, as a consequence of the safety shield 8 having moved to its activation position, the push button 29 is now allowed to move distally with respect to the housing 12 and the peg 31 of the push button 29 comes in abutment against the flexible tooth 18 of the inner cylinder 15, said flexible tooth 18 being thereby caused to deflect radially outwardly. As a consequence, the radial stop 22 of the piston rod 21 disengages from the proximal abutment surface 18a of the flexible tooth 18 of the inner cylinder 15 and the second helical spring 34 is freed.

The second helical spring 34 tends to come back to its expanded state and causes the distal movement of the piston rod 21. The piston rod 21 comes in abutment on the piston 7. The friction force of the piston 7 against the inner walls of the container 2 being higher than the force of the second helical spring 34, the container 2 is also caused to move distally under the effect of the expansion of the second helical spring 34.

As shown on FIG. 4, the distal movement of the container 2 causes the insertion of the needle 6 in the injection site 4. At the same time, and as a consequence of the same movement, the distal sloping surface 27 of the second ring 25 has come in abutment on the proximal sloping surface 26b of the first ring 24, causing the flexible tooth 26 to deflect inwardly radially and to disengage from the radial stop 14 of the housing 12, as shown on FIG. 4. As a consequence, said first ring 24 is freed from said housing 12. The first ring 24 is no more coupled to the housing 12 in the distal direction. Moreover, in this insertion position, the distal face 24b of the first ring 24 is in abutment against the radial rim 9 of the safety shield 8: as a consequence, the first ring 24 is now coupled to the safety shield 8 in the proximal direction under the biasing force of the first helical spring 33. The first helical spring 33 is now in a compressed state and the container 2 is thereby caused to be stopped at a predetermined insertion depth. The second helical spring 34 in the example shown, acts as automatic injection means.

The force of the second helical spring 34 is therefore allowed to overcome the friction force of the piston 7 against the inner walls of the container 2 and the piston rod 21 is caused to push the piston 7 distally so as to realise the injection, as shown on FIG. 5.

At the end of injection, as shown on FIG. 5, the flexible tooth 26 of the first ring 24 is still disengaged from the radial stop 14 of the housing 12. As a consequence, when the user withdraws the device 1 from the injection site, the first helical spring 33, which is now coupled to the safety shield 8 in the distal direction, is free to expand and deploy the safety shield 8 over the needle 6 (step not shown); the safety shield 8 is therefore in its safety position, distally spaced from its rest position, and in which it covers the needle 6 thereby preventing any needle stick injury. The device of the invention is therefore particularly safe.

As can be noticed from FIG. 4, the flexible tooth 26 is disengaged from the radial stop 14 of the housing 12 as soon as the injection starts. As a consequence, if the user inadvertently withdraws the device 1 of the invention from the injection site 4 before the end of the injection, the safety shield 8 will automatically expand over the needle 6 and will prevent any needle stick injury.

The device of the invention provides for a very safe device, which cannot be triggered as long as it is not correctly located at the injection site and which does not hurt the user during the step of deactivating the safety system. In particular, because of the presence of specific isolating means, the user does not feel the force of the biasing means intended to expand the safety shield at the end of injection.

The injection device of the invention also allows automatic injection of a product to be performed by a patient without any risk of needlestick injury, before, during and after use. In particular, the safety shield of the device of the invention is in its active state right at the end of the insertion step, before the injection step actually begins. In this way, even if the patient decides to withdraw the device before the end of the injection, then the safety shield automatically extends over the needle.

What is claimed is:

1. A device for automatic injection of a product into an injection site, the product being carried by a container having an open proximal end and a substantially closed distal end and carrying a needle to provide an outlet port for the product from the container, and a piston provided in the container and movable with respect to the container, the distal movement of the piston causing the product to be expelled from the container through the needle, the device comprising:

a housing receiving at least partially said container, said container being movable with respect to said housing between an initial position, in which a tip of the needle does not extend beyond a distal end of said housing, and an insertion position, distally spaced relative to said initial position, and in which the tip of the needle extends beyond said distal end of said housing;

a safety shield coupled to said housing and movable with respect thereto between a rest position, an activation position, proximally spaced relative to said rest position, and a safety position, distally spaced with respect to said rest position;

biasing means for causing the movement of said safety shield to said safety position;

triggering means for causing the container to move from its initial position to its insertion position, said triggering means being releasable by movement of said safety shield to said activation position; and, isolating means for isolating said safety shield from said biasing means when said safety shield is moved to its activation position, wherein said isolating means includes a first ring, receiving said container, said first ring being coupled to said biasing means in the proximal direction and coupled to said housing in the distal direction, and being independent from said safety shield before said safety shield is in its activation position.

2. A device according to claim 1, wherein said first ring comprises at least a flexible tooth provided with a distal abutment surface and said housing comprises at least a radial stop, said first ring being coupled to said housing in the distal direction by means of said distal abutment surface resting on said radial stop, when said safety shield is moved to its activation position.

3. A device according to claim 2, wherein said device further comprises a second ring, said second ring being fixed to the proximal region of said container and being proximally spaced with respect to said first ring when said safety shield is moved to its activation position, said biasing means comprising a helical spring, a proximal end of said helical spring bearing on a part of said second ring and a distal end of said helical spring bearing on a part of said first ring.

4. A device according to claim 3, wherein said flexible tooth comprises a sloping surface and said second ring comprises a distal sloping surface, said distal sloping surface being capable to come in abutment against said sloping surface so as to deflect said flexible tooth and disengage said flexible tooth from said radial stop, thereby freeing said first ring from said housing when said container is in its insertion position.

5. A device according to claim 4, wherein said safety shield comprises at least one radial rim, said radial rim being located in regards to the distal face of said first ring, said distal face of said first ring coming in abutment against said radial rim when said container is in its insertion position, thereby coupling said first ring to said safety shield in the distal direction under the biasing force of the biasing means.

* * * * *

UNITED STATES PATENT AND TRADEMARK OFFICE
CERTIFICATE OF CORRECTION

PATENT NO.       : 8,696,628 B2
APPLICATION NO.  : 13/120676
DATED            : April 15, 2014
INVENTOR(S)      : Guillaume Grunhut It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 321 days.

Signed and Sealed this
Twenty-ninth Day of September, 2015

Michelle K. Lee
*Director of the United States Patent and Trademark Office*